United States Patent [19]

Farrell

[11] Patent Number: 5,107,007

[45] Date of Patent: Apr. 21, 1992

[54] BIS-PLATINUM COMPLEXES AS CHEMOTHERAPEUTIC AGENTS

[75] Inventor: Nicholas Farrell, Winooski, Vt.

[73] Assignee: The University of Vermont and State Agricultural College, Burlington, Vt.

[21] Appl. No.: 401,919

[22] Filed: Sep. 1, 1989

[51] Int. Cl.$^5$ ............................................. C07F 15/00
[52] U.S. Cl. ..................................... 556/137; 556/136
[58] Field of Search .................. 556/136, 137, 24; 514/187, 492, 188; 544/225; 546/4, 5, 6; 548/103

[56] References Cited

U.S. PATENT DOCUMENTS

| | | | |
|---|---|---|---|
| 4,533,502 | 8/1985 | Rochon et al. | 556/137 X |
| 4,560,782 | 12/1985 | Papageorgiou et al. | 556/137 |
| 4,565,884 | 1/1986 | Andrulis, Jr. et al. | 556/137 |
| 4,730,069 | 3/1988 | Kolar et al. | 556/137 |
| 4,797,393 | 1/1989 | Farrell et al. | 556/137 |

Primary Examiner—Arthur C. Prescott
Attorney, Agent, or Firm—Burns, Doane, Swecker & Mathis

[57] ABSTRACT

A bis(platinum) complex having the structure:

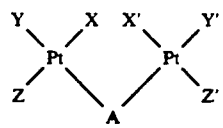

wherein X, Y, Z, X', Y', and Z' are the same or different ligands and are halide, sulphate, phosphate, nitrate, carboxylate, substituted carboxylate, dicarboxylate, substituted dicarboxylate primary or secondary amine, sulfoxide, phosphine, pyridine-type nitrogen and the like; preferably, there is at least one Pt-anion bond on each Pt molecule; and A is a diamine or polyamine.

Complexes of trans geometry $[PtX_2(L)(L')]$ where at least L is a planar ligand such as pyridine but preferably quinoline and L' may be amine, sulfoxide or substituted sulfoxide and X is a chloride, nitrate or carboxylate.

A process for obtaining bis(platinum) complexes where the two platinum coordination spheres may contain different ligands in each sphere and where the geometry of each platinum coordination sphere may be the same or different.

17 Claims, 1 Drawing Sheet

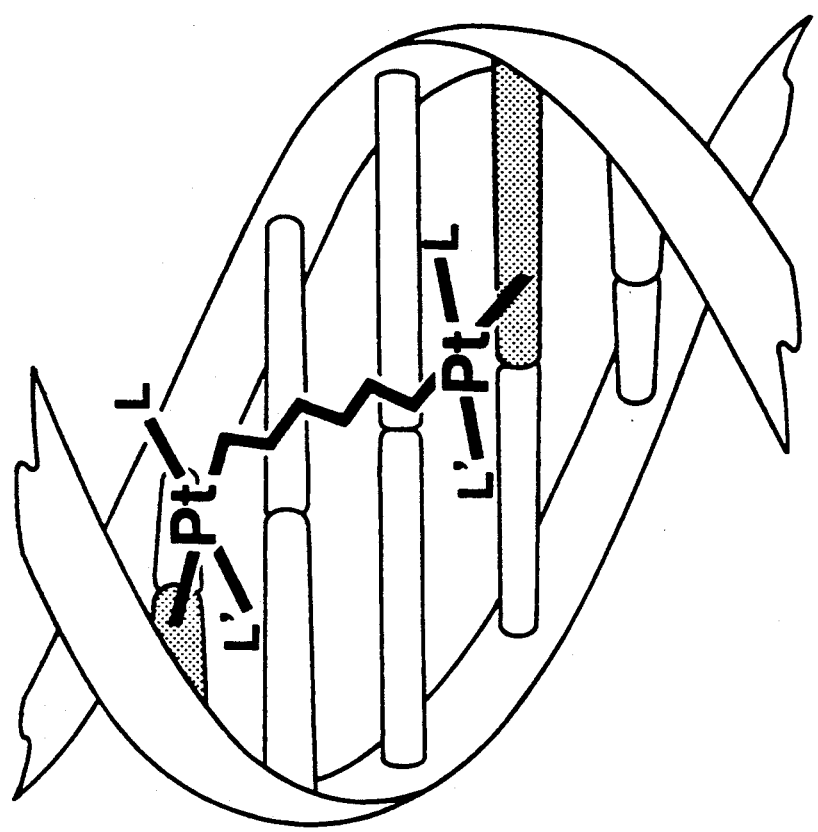

BIS-PLATINUM COMPLEXES AS CHEMOTHERAPEUTIC AGENTS

BACKGROUND OF THE INVENTION

The present invention relates to novel bis(platinum) complexes and to pharmaceutical compositions containing them.

The use of platinum complexes in cancer chemotherapy is well known. A number of platinum complexes, such as Platinol, a registered trademark of cisplatin manufactured by Bristol Myers, Co., are used to treat testicular, ovarian, head and neck, and small-cell lung carcinomas. However, treatment with cisplatin may result in severe nephrotoxicity. A further clinical disadvantage is the problem of acquired drug resistance resulting in the tumor becoming refractory to treatment by the agent.

To overcome the nephrotoxic effects of cisplatin, a second-generation analog, carboplatin, was developed. Paraplatin is a registered trademark for carboplatin manufactured by Bristol-Myers, Co. Carboplatin, or [Pt(NH$_3$)$_2$(CBDCA)](where CBDCA is 1,1'cyclobutanedicarboxylate), is effective against the same spectrum of carcinomas as cisplatin, but exhibits a marked reduction in the nephrotoxic effects.

A number of different platinum compounds have been developed in an attempt to treat different tumors or carcinomas. For instance, U.S. Pat. No. 4,225,529 discloses the use of a cis coordination compound of platinum having four ligands which are selected from the group consisting of halides, sulphates, phosphates, nitrates, carboxylates, and same or different straight-chain amines which are coordinated to the platinum atom through their nitrogen atoms. These complexes are utilized for treating L-1210 leukemia in mice.

Also, U.S. Pat. Nos. 4,250,189, 4,553,502, and 4,565,884 relate to various Pt(II) and Pt(IV) complexes having antitumor activity. These bis(platinum) complexes are linked with a carboxylate linkage such that upon administration of these complexes to the patient, the complexes undergo rapid hydrolysis to produce two cis monoplatinum moieties which are then delivered to the active site.

However, in U.S. Pat. No. 4,797,393, a bis(platinum) complex is disclosed, which complex is delivered intact to the active site. This bis(platinum) complex has a bridging diamine or polyamine ligand and has primary or secondary amines or pyridine type nitrogens attached to the platinum complex, as well as two different or identical ligands which may be a halide, sulphate, phosphate, nitrate, carboxylate, substituted carboxylate or dicarboxylate.

Most of the synthesis of platinum analogs to date has been based on the [cis-Pt(amine)$_2$X$_2$] structure where X is a chloride or an anionic leaving group since it is believed that the cis configuration is necessary for antitumor activity in monomeric platinum complexes. A wide range of amines has been employed and a major emphasis has been on 1,2-diaminocyclohexane (which is oftentimes referred to as "dach") because laboratory studies (Burchenal et al. *Biochimie*, 1978, 60, 961) show that complexes derived from these amines are non-cross-resistant with cisplatin. This means that dach complexes maintain their curative activity in tumor cell lines resistant to cisplatin and the clinical advantage of such an agent should be apparent. The mechanism of action of cisplatin is generally believed to be by formation of crosslinks, especially interstrand crosslinks on DNA, producing an overall conformational change on the DNA, which eventually leads to the inhibition of replication and thus produces a cytotoxic effect as discussed in Sherman and Lippard, *Chem. Review*, 1987, 87, 1153 and Reedijk et al, *Structure and Bonding*, 1987, 67, 53.

Even though other closely related platinum complexes such as those in the trans-configuration [trans-Pt(NH$_3$)$_2$X$_2$], trans-DDP, and monodentate complexes [(Pt(NH$_3$)$_3$Cl]$^+$ and [Pt(dien)Cl]$^+$, (dien=diethylenetriamine, a tridentate amine) do bind to DNA, they do not exhibit antitumor activity. This is because the trans-[Pt(NH$_3$)$_2$Cl$_2$] and especially monodentate species such as [Pt(NH$_3$)$_3$Cl]$^+$ cannot form the 1,2-intrastrand crosslink.

It has been discovered that bis(platinum) complexes of U.S. Pat. No. 4,797,393 may exhibit high cytotoxic activity and are non-cross-resistant with both cisplatin and platinum-dach complexes. Their DNA binding involves interstrand crosslinks formed because of the bimetallic nature of the bis(platinum) complexes whereby each platinum atom of the bis(platinum) unit binds to opposite DNA strands. This effect has led in part to the discovery of structurally new bis(platinum) derivatives which also have activity in cisplatin-resistant lines and thus may have a broader spectrum of activity than cisplatin. Thus, there remains a need in the art to produce pharmaceutical compounds which are active in cisplatin-resistant lines.

SUMMARY OF THE INVENTION

Accordingly, it is an object of the present invention to provide a process for producing stable bis(platinum) complexes to be used for antitumor and pharmaceutical applications.

It is another object of the present invention to produce bis(platinum) complexes that induce interstrand crosslinks to the DNA molecule.

It is yet another object of the present invention to provide a bis(platinum) complex having at least one Pt—Cl bond on each platinum, such that each Pt atom of the bis(platinum) molecule may bind to opposite strands of DNA.

A still further object of the present invention is to provide a bis(platinum) complex in cis or trans isomeric form that exhibits antitumor activity.

A further object is to demonstrate the activation of monomeric trans complexes which exhibit cytotoxicity equivalent to cisplatin and which may exhibit enhanced antitumor activity by themselves or upon incorporation into the new bis(platinum) structures.

A further object is to demonstrate a method for obtaining bis(platinum) complexes where the two platinum coordination spheres are different by using as a precursor a monomeric platinum complex containing only one end of a diamine bound to the platinum.

In accordance with the foregoing objectives, the present invention provides a bis(platinum) complex having the general formula:

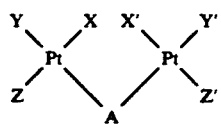

wherein X, Y, Z, X', Y' and Z' may be a combination of anionic groups or neutral groups and A is a bridging ligand.

These and other objects, features and advantages will be apparent from the following more particular description of the preferred embodiments.

BRIEF DESCRIPTION OF THE DRAWING

The FIGURE depicts the formation of an interstrand crosslink through binding of one Pt of the bis(platinum) molecule to at least one base on one strand of DNA with concomitant binding of the other Pt atom to a base on the other strand.

DESCRIPTION OF THE PREFERRED EMBODIMENT

The present invention relates to novel bis(platinum) complexes and to the preparation of these complexes. These novel platinum complexes have coordination spheres which may be monodentate and thus contain only one anionic group, such as a chloride ion, attached to each platinum atom or the platinum coordination spheres may be different and may contain, for example, either one or two anionic groups, such as chloride, in each sphere. Further, the geometry of the coordination spheres may be cis or trans or a mixture thereof; that is, one coordination sphere may be cis and the other may be trans.

A general formula of the bis(platinum) complexes encompassed in the present invention include:

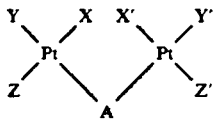

wherein X, Y, Z, X', Y', and Z' may be a combination of anionic groups such as halides including chlorine, bromine, iodine and fluorine and pseudohalides, as well as sulphate, phosphate, phosphonate, nitrate, carboxylate, substituted carboxylated, dicarboxylate and substituted dicarboxylate, or any neutral group such as a primary or secondary amine, sulfoxide (such as DMSO), phosphine, pyridine, or planar aromatic or pseudo-aromatic pyridine-like ligand such as substituted pyridine, quinoline, imidazole, thiazole, pyrimidine, purine, acridine, pyrazole, benzimidazole, benzothiazole and the like, as well as sulfoxide and phosphine. It is preferable to use at least one chloride group per platinum atom. Where there is only one anionic group attached to each Pt atom, each Pt atom is monodentate and the complexes carry an overall 2+ charge. Where there is one anionic group attached to one Pt atom and two to the second Pt atom; the complexes therefore carry a 1+ charge, with one Pt atom monodentate and the other bidentate.

The bridging ligand A is a diamine or polyamine wherein the primary amine N atoms are coordinated to the Pt atom such that platinum is present as Pt$^{2+}$ and preferably has the formula:

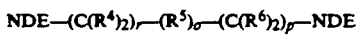

in which r and p are integers from 1 to 4, inclusive and o is 0 or 1; and the R$^4$ and R$^6$ groups are the same or different and are hydrogen, lower alkyl, aryl, cycloalkyl, cycloalkenyl, aralkyl, halogen, pseudohalogen, hydroxy, alkoxy, aryloxy, carboxylic acid ester, or carboxylic acid salt. Preferably, all R$^4$ and R$^6$ groups are hydrogen.

The R$^5$ group is optional, and if employed is selected from alkyl, aryl (such as phenyl), amino, alkylamino, diamino of the formula:

wherein q is an integer of 1 to 4, inclusive, hydroxyalkyl, alkoxy, sulfur or oxygen.

The D and E groups are the same or different and are selected from hydrogen, lower alkyl, aryl, alkaryl, aralkyl, alkenyl, cycloalkyl, cycloalkenyl, halogen, pseudohalogen, hydroxy, alkoxy, aryloxy, or sulphonic acids or salts thereof. The preferred substitutent is hydrogen.

Particularly preferred A bridging ligands include straight chain diamines. Such bis(platinum) complexes preferably have the formula:

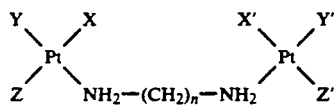

wherein X, Y, Z, X', Y' and Z' may each be represented by the groups set forth above and n is represented by 2 to 20 and preferably 4 to 12, inclusive.

The sulfoxide preferably has the structure

where each R is a straight chain or branched alkyl group having one to 12 carbon atoms. The sulfoxide substituent may optionally be substituted preferably with an aromatic, e.g., aryl or alkaryl, group.

The amines may be aliphatic or aromatic and generally include ammonia, branched or straight chain lower alkyl amines, aryl amines, aralkyl amines, lower alkenyl amines, cycloalkyl amines, cycloalkenyl amine, and polycyclic hydrocarbon amines.

Substituted or unsubstituted heterocyclic amines, nucleosides, nucleotides, pyridine-type nitrogen containing compounds, and the like may be used in the practice of the present invention. Suitable substituents include but are not limited to alkyl, aromatic aryl, hydroxy, lower alkoxy, carboxylic acid or acid ester, nitro and halogen substituents.

Purines and pyrimidines which are suitable in the practice of the present invention include, for example, cytosine, uracil, thymine, guanine, adenine, xanthine, hypoxanthine, purine, pyrimidine and their substituted derivatives.

Where the anionic group is a carboxylate or a substituted carboxylate, the anionic group may be represented by the formula:

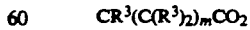

wherein m is an integer from 0 to 5, inclusive. The R$^3$ groups may be the same or different and may be hydrogen, substituted or unsubstituted straight or branched chain alkyl, aryl, alkaryl, alkenyl, cycloalkyl, cycloalkenyl, halogen, pseudohalogen, hydroxy, carbonyl, formyl, nitro, amido, amino, alkoxy, aryloxy, sulphonic acid salt, carboxylic acid ester or carboxylic acid salt.

Furthermore, the $R^3$ groups can be combined so that two $R^3$ groups represent a double bond oxygen or sulphur atom.

Lower alkyl and lower alkenyl in the present specification means one to five carbon atoms. Unless indicated otherwise, alkyl or alkenyl means 1 to 12 carbon atoms. By cycloalkyl is meant chains of 3 to 10 carbon atoms. Substituted in the present specification, unless indicated otherwise, is intended to mean substitution with a group chosen from alkyl, aryl, cycloalkyl of 3 to 10 carbon atoms, cycloalkenyl, aralkyl, halogen, pseudohalogen, hydroxy, alkoxy, cycloamino, or carboxylic acid salts or esters of one to ten carbon atoms.

The term pseudohalide in the present invention has the meaning found on page 560 of "Advanced Inorganic Chemistry" by Cotton and Wilkinson, Interscience Publishers, 1966. The text describes a pseudohalogen, i.e., pseudohalide, as being a molecule consisting of more than two electronegative atoms which, in the free state, represent halogen atoms. Examples of these molecules include cyanide, cyanate, thiocyanate, and azide.

Preferably, there are one or two chlorine atoms on each Pt atom; thus, a total of two to four chlorine atoms are present on the preferred compounds of the present invention.

The bis(platinum) complexes of the present invention may contain a platinum moiety in the trans configuration, as well as the monodentate bis(platinum) complex. These complexes differ from the monomeric platinum complexes in that the mechanism of binding to DNA is different. The principal adducts of cisplatin, for example, are the intrastrand crosslinks between adjacent guanines (GG), and between a guanine-adenine neighboring pair (GA). The cytotoxic effect is believed to be induced by the conformational change of the DNA due to the Pt binding. Complexes such as trans-[Pt(NH$_3$)$_2$Cl$_2$] and the monodentate species such as [Pt(NH$_3$)$_3$Cl]$^+$ have no cytotoxic effect presumably because their binding precludes any intrastrand crosslinking, even though they bind avidly to the DNA molecule.

In contrast to monomeric complexes, the bis(platinum) derivatives of U.S. Pat. No. 4,797,393 are able to bind to the DNA molecule by two principal methods: an intrastrand crosslink formed in the same manner as described above and also an interstrand crosslink caused by each unique Pt atom binding to the two strands of the DNA molecule. See the FIGURE. The schematic depicts four base pairs, however, the base pair separation is schematic and is not intended to be restricted to the separation depicted. In the FIGURE, L and L' are any ligands on the platinum which are not directly involved with the initial interstrand crosslink formation. The complexes of the present invention cannot, by nature of their structure, form intrastrand links on both Pt atoms but the agents remain highly cytotoxic, especially in cisplatin-resistant lines. This is despite the fact that the monomeric precursors of monodentate or trans geometry exert no cytotoxic effect. The combination of these units, however, into a bis(platinum) complex of the general formula disclosed herein, results in significant cytotoxicity. The dominant and uniting feature of all these new bis(platinum) complexes is their ability to induce interstrand crosslinking and the formation of at least one Pt-nucleic acid base bond on each strand of DNA. These features appear to be a sufficient requisite for cytotoxicity. Thus, the bimetallic agents forming interstrand crosslinking between the DNA strands are excellent chemotherapeutic agents, especially for those tumors which are resistant to cisplatin.

The bis(platinum) complexes according to the present invention are intended for pharmaceutical application. The complex is useful for the identical diseases and modalities and use in the same patients as cisplatin. This includes the treatment of tumors, radiation sensitization or potentiation (Douple et al, *Cisplatin Current Status and New Developments*, Eds. A. W. Prestayko, S. T. Crooke, and S. K. Carter, Academic Press, 125 (1980); Douple, *Platinum Metals Rev.*, 1985, 29, 118), and parasitic diseases such as sleeping sickness (Farrell et al, *Biochem. Pharmacology*, 1984, 33, 961). The complexes of the present invention are administered at approximately the same dosage levels as cisplatin, while taking into account their LD$_{50}$ values. The complex is normally associated with a suitable pharmaceutical carrier. For example, the complex and carrier can be formulated for parenteral or oral administration by methods known in the art. For instance, see *Remington's Pharmaceutical Sciences* for suitable pharmaceutically acceptable carriers and formulation methods.

The present invention also discloses a process for producing a bis(platinum) complex by use of monomeric precursors which contain a diamine or polyamine bound to the platinum atom by one of the amines, the other being uncomplexed (free or dangling). Reaction of these precursors with additional molecules containing at least one chloride ion capable of being displaced will give bis(platinum) complexes whose structure will depend on both the exact structure of the precursor molecule and the molecule to be appended. Specific examples are those of Examples 3 and 4 set forth below. The bridging and therefore bis(platinum) complex formation occurs through substitution by the free amino end of the precursor molecule of a Pt—Cl bond on the appended molecule. The precursor molecules are most simply represented as RNH$_3$+Cl and reaction with the selected molecule gives the reaction:

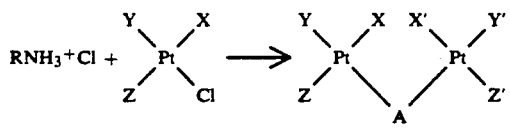

where RNH$_3$ represents PtX'Y'Z'A wherein Z', Y', Z' and A as well as X, Y and Z are as defined above. In the case of Example 3, the reaction is:

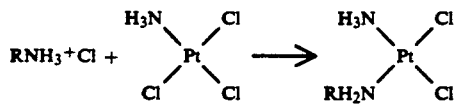

where R is trans-[PtCl$_2$(NH$_3$)H$_2$N(CH$_2$)$_4$]-. See Reaction Scheme 2.

The reaction is preferably carried out in aqueous or methanolic solution in presence of a base. In the case of Example 3, the product precipitates from solution, is filtered off and recrystallized by standard methods known in the art.

In order to fully illustrate the present invention and the advantages thereof, the following specific examples are given, it being understood that these examples are intended only to be illustrative without serving as a limitation on the scope of the present invention.

The examples describe the preparation of the new bis(platinum) complexes and precursors for new bis(platinum) complexes by reaction with the starting materials of cis[PtCl$_2$(NH$_3$)$_2$] and K[PtCl$_3$(NH$_3$)] respectively. The cis-[PtCl$_2$(NH$_3$)$_2$] compound is prepared by the general method of Dhara, *J. Indian Chem.*, 1970, 8, 913, while the K[PtCl$_3$(NH$_3$)] compound is prepared by the general method of Abrams et al, *Inorg. Chim. Acta*, "A Convenient preparation of the Amminetrichloroplatinate(II) Anion" 1987, 3, 131.

EXAMPLE 1

Preparation of [{trans-[PtCl(NH$_3$)$_2$]$_2$H$_2$N(CH$_2$)$_n$NH$_2$]Cl$_2$

Monomeric trans-[PtCl$_2$(NH$_3$)$_2$] was prepared from the tetra-amine complex by reacting cis-[PtCl$_2$(NH$_3$)$_2$] with aqueous ammonia (NH$_3$) to form an intermediate, [Pt(NH$_3$)$_4$]Cl$_2$. This intermediate was further reacted with an aqueous hydrochloric acid solution to form trans-[PtCl$_2$(NH$_3$)$_2$]. Trans-[PtCl$_2$(NH$_3$)$_2$] was reacted with 1,4-butanediamine in H$_2$O and stirred overnight. The clear solution was then filtered, evaporated to dryness and recrystallized from H$_2$O/acetone or H$_2$O/EtOH to give [{trans-PtCl(NH$_3$)$_2$}$_2$H$_2$N(CH$_2$)$_4$NH$_2$]Cl$_2$. The complex was characterized by elemental analysis as noted in Table 1 below, $^1$H NMR (rel. to TMS) at 2.74 and 1.79 ppm and $^{195}$Pt NMR at $-2436.7$ ppm rel. to PtCl$_6^{2-}$. The IR spectrum (KBr disc) shows bands typical of bridging diamine and v(Pt—Cl)=330 cm$^{-1}$.

Examples of other trans complexes which may be used in this way include species such [PtCl$_2$(pyridine)$_2$], trans[PtCl$_2$(pyridine)(NH$_3$)], trans-[PtCl$_2$(pyridine)(DMSO)], [PtCl$_2$(quinoline)(DMSO)], [PtCl$_2$(isoquinoline)(DMSO)]. The present inventor has also disclosed that the presence of a planar ligand such as pyridine or quinoline dramatically improves the cytotoxicity of complexes of the trans configuration. Table III presents the in vitro data with comparison of some NH$_3$ complexes. As will be seen, a complex such as trans-[PtCl$_2$(pyridine)$_2$] is in fact as cytotoxic as cisplatin and represents a further class of complexes non-cross-resistant with the parent cisplatin.

Thus, a further extension of the present discovery is the demonstration of the activation of trans complexes by use of planar ligands rather than NH$_3$. The general formula for cytotoxic trans complexes with planar ligands is [PtX$_2$(L)(L′)] where X may be any anionic group and L and L′ are the planar ligand such as pyridine, quinoline, isoquinoline, acridine, pyrazole, thiazole, imidazole, benzimidazole, benzothiazole, and other pyridine-like planar aromatic or pseudo-aromatic heterocycles. Where L is not the same as L′ and L represents the planar ligand as above, then L′ may represent a primary or secondary amine such as NH$_3$ or a sulfoxide such as DMSO. Incorporation of these structures into bis(platinum) complexes will occur in the same manner as outlined for trans[PtCl$_2$(NH$_3$)$_2$].

EXAMPLE 2

Preparation of Trans-[PtCl$_2$(NH$_3$)(H$_2$N(CH$_2$)$_4$NH$_3$)]Cl

This example demonstrates the preparation of a metal complex containing only one end of the diamine initially bound. The preparative scheme for the precursor is outlined in Reaction Scheme 1 and is adapted from Farrell and Qu, *Inorg. Chem.*, Chemistry of Bis(platinum) Complexes, "Formation of trans derivatives from tetra-amine complexes," In press, September 1989. The precursor, trans-[PtCl$_2$(NH$_3$)H$_2$N(CH$_2$)$_4$NH$_3$]Cl was prepared by Steps 1 and 2 of Scheme 1 and the precursor complex is Product 2c. Product 2c contains one end of the diamine bound to the platinum and the other end free (or dangling). The free or dangling end of the diamine may then be used to produce new bis(platinum) complexes, as shown in Reaction Scheme 2. In Reaction Scheme 2, the free amine end is used to bind to another platinum atom but it may also be used to bind another metal.

The preparation is outlined below:

Step 1 of Reaction Scheme 1, 0.6 grams or 2 mmol of cis-[PtCl$_2$(NH$_3$)$_2$] was suspended in 20 ml of water and 0.177 grams or 2 mmol of 1,4-diaminobutane was added. This mixture was then stirred at 60° C. for 1–1.5 hours. The solution was then filtered and evaporated to 1 ml. The product was precipitated by refrigeration at 3° C. for about 24 hours. The precipitated product was then filtered, washed with EtOH and dried. The complex was further recrystallized from H$_2$O/EtOH. The yield was about 68% for the product [{cis-Pt(NH$_3$)$_2$(H$_2$N(CH$_2$)$_4$NH$_2$)}$_2$]Cl$_4$ (Compound 2a).

Step 2 of Reaction Scheme 1) 0.5 grams of Complex 2a, [{cis-Pt(NH$_3$)$_2$(H$_2$N(CH$_2$)$_4$NH$_2$)}$_2$]Cl$_4$ or 0.64 mmol was dissolved in 2 ml H$_2$O and 50 ml 6N HCl was then added. The solution was allowed to react for 6–8 hours at 60°–70° C. and was stirred constantly during that period. A yellow solid precipitate then formed, which was filtered off and washed with H$_2$O/acetone and further dried in vacuo. The filtrate was recrystallized from DMA/0.1 N HCl. The yield for the product [{trans-PtCl$_2$(NH$_3$)}$_2$H$_2$N(CH$_2$)$_4$NH$_2$] was about 48% (Product 2b). The IR spectrum showed bands at v(NH) =3280, 3235, 3195 cm$^{-1}$, v(Pt-Cl)=340 cm$^{-1}$. The $^1$H NMR in d$_7$-DMF gave peaks at 1.63, 2.68 ppm and the $^{195}$pt NMR gave a peak at $-2167$ ppm.

REACTION SCHEME 1

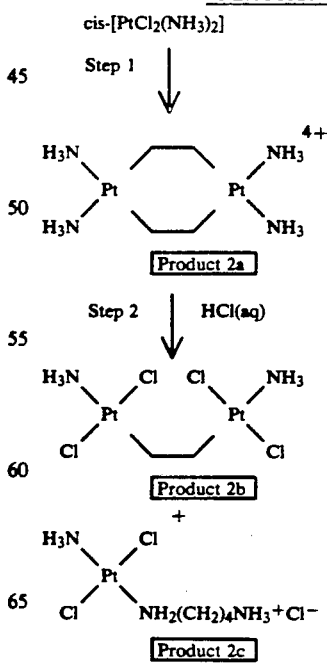

REACTION SCHEME 2

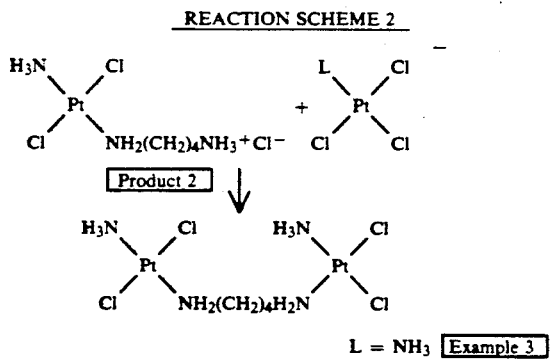

L = NH₃ [Example 3]

or

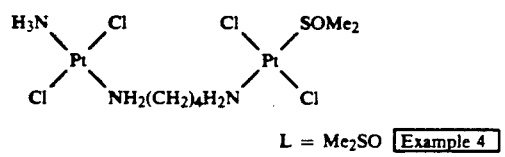

L = Me₂SO [Example 4]

The trans-[PtCl₂(NH₃)(H₂N(CH₂)₄NH₃)]Cl complex was isolated by evaporation of the above filtrate to an oil, upon filtering off Product 2b. Approximately 30 ml of EtOH was then added to the oil and the solution was stirred for approximately 30 minutes. A yellow solid was formed and filtered off. The filtrate was then washed with EtOH and dried. Trans[PtCl₂(NH₃)(H₂N(CH₂)₄NH₃)]Cl was then recrystallized from H₂O/EtOH (Product 2c). The IR spectrum shows bands corresponding to ν(NH) at 3290(sh), 3245, 3200 and ν(Pt—Cl) at 335 cm$^{-1}$. The $^1$H NMR in D₂O gave peaks at 1.8, 2.72(t) and 3.1 ppm. The $^{13}$C NMR in D₂O gave four peaks at 47.8, 42.0, 29.6 and 26.8 ppm. The $^{195}$Pt NMR gave a peak at −2132 ppm.

EXAMPLE 3

Formation of bis(platinum) complexes with the platinum coordination spheres in different geometries Preparation of
[{trans-PtCl₂(NH₃)}H₂N(CH₂)ₙNH₂{cis-PtCl₂(NH₃)}]

This procedure demonstrates the use of a metal complex containing only one end of the diamine initially bound and the subsequent platination of the free or dangling amine end to produce bis(platinum) complexes (Reaction Scheme 2). To the precursor, trans-[PtCl₂(NH₃)(H₂N(CH₂)₄NH₃)]Cl (Compound 2c), one equivalent of K[PtCl₃(NH₃)] in MeOH was added in the presence of triethylamine. The complex of [{cis-PtCl₂(NH₃)}H₂N(CH₂)₄ NH₂{trans-PtCl₂(NH₃)}] precipitated out of solution, was filtered, washed with water and acetone and dried. The new complex was characterized by elemental analysis: $^1$H NMR and $^{195}$Pt NMR(−2165 ppm and −2171 ppm).

EXAMPLE 4

Formation of bis(platinum) complexes with two different coordination spheres

Preparation of
[trans-{PtCl₂(Me₂SO)(H₂N(CH₂)₄NH₂)trans-[PtCl₂(NH₃)}]

Following the same procedure set forth in Example 2, the precursor, trans-[PtCl₂(NH₃)(H₂N(CH2)₄NH₃)]Cl, was prepared as a source of an amine for binding. This precursor was then reacted with one equivalent of K[PtCl₃(Me₂SO)] anion in MeOH in the presence of triethylamine. The precipitate was then filtered, washed with water and acetone, and dried. The specific structure formed from this procedure was [trans{PtCl₂(Me₂SO)(H₂N(CH₂)₄NH₂)trans-[PtCl₂(NH₃)}]. The new complex was characterized by elemental analysis, IR spectrum ν(Pt—Cl)=330, ν(SO)=1115, ν(NH)=3260, 3200, 3110 cm$^{-1}$, $^1$H NMR=3.5, 1.85, and 2.65 ppm $^{195}$pt NMR(−2172 and −3131 ppm ).

SUMMARY OF PROPERTIES OF NEW BIS(PLATINUM) COMPLEXES

The complexes as prepared in the preceding examples were readily soluble in dimethylsulfoxide (DMSO), dimethylformamide (DMF), and had good water solubility when isolated as cationic complexes. The data in Table I below summarizes the elemental analyses obtained for the complexes derived from the procedures set forth above.

TABLE I

| | ELEMENTAL ANALYSES FOUND (CALCULATED) | | | |
|---|---|---|---|---|
| EXAMPLE | % C | % H | % N | % Cl |
| 1 | 7.76 (7.74) | 3.61 (3.68) | 12.0 (12.04) | 20.11 (20.32) |
| 3 | 7.13 (7.34) | 2.63 (2.77) | 8.49 (8.56) | 21.79 (21.68) |
| 4 | 10.59 (10.07) | 2.93 (2.96) | 5.65 (5.87) | 20.40 (19.83) |

EXAMPLE 5

Biological Activity

The monodentate bis(platinum) complexes, Example 1, and the platinum moiety containing one trans configuration on one Pt atom, and a cis anion configuration on the other Pt atom, Example 3, were tested for cytotoxic activity in various L-1210 murine leukemia cell lines. The tests were carried out in vitro according to the procedures outlined by M. P. Hacker et al in Cancer Research, 1985, 45, 4748. The term ID₅₀ refers to the concentration required to inhibit cell growth by 50%, and thus the lower the number, the more effective cytotoxin that particular agent. The bis(platinum) complexes of the present invention were compared to bis(platinum) complexes of equal chain length having only cis configurations and a typical monodentate monomeric complex [Pt(dien)Cl]Cl. Table II summarizes the results obtained.

TABLE II

| | CYTOTOXICITY DATA | | | |
|---|---|---|---|---|
| COMPLEX | L-1210/0 ID₅₀ uM | L-1210/ DDP ID₅₀ uM | L-1210/ dach ID₅₀ | Solvent |
| Example 1 | 3.4 | 0.9 | 5.4 | H₂O |
| Example 3 | 0.76 | 3.36 | 2.6 | 10% DMSO |
| BisPt4 | 0.28 | 2.19 | 0.336 | DMF |
| BisPtmal | 0.93 | 5.03 | 2.55 | H₂O |
| [Pt(dien)Cl]Cl | >20 | >20 | >20 | H₂O | wherein
Example 1=[{trans-[PtCl(NH₃)}₂H₂N(CH₂)₄NH₂]Cl₂
Example 3=[{cis-PtCl₂(NH₃)}H₂N(CH₂)₄NH₂{trans-PtCl₂(NH₃{]
BisPt4=[{cis-PtCl₂(NH₃)}₂(H₂N(CH₂)₄NH₂)]

BisPtmal = [{cis-Pt(mal)(NH₃)}₂(H₂N(CH₂)₄NH₂)]

As can be seen from the data, the complexes of the present invention maintain high activity in the L-1210/DDP line which is resistant to cisplatin. Furthermore comparison of Example 1 with [Pt(dien)Cl]Cl shows that the monomeric complex is totally inactive, in accord with accepted theories, yet the combination of two monodentate units into a bis(platinum) complex as in Example 1 produces highly active cytotoxic agents.

TABLE III

Toxicity of Complexes of General Formula [PtCl₂LL']

| L | L' | Geometry | ID₅₀ (μM) L-1210/O | L-1210/DDP |
|---|---|---|---|---|
| py | py | trans | 0.61 | 0.80 |
| py | py | cis | 8.96 | 12.5 |
| py | DMSO | trans | 6.62 | 5.67 |
| Meim | DMSO | trans | 6.57 | 10.33 |
| quin | DMSO | trans | 0.4 | 1.57 |
| iso-quin | DMSO | trans | 2.75 | 1.17 |
| NH₃ | DMSO | cis | >20 | >20 |
| NH₃ | DMSO | trans | >20 | >20 |
| NH₃ | NH₃ | cis | 0.2 | 8.0 |
| NH₃ | NH₃ | trans | >20 | >50 | where py=pyridine; quin=quinoline; isoquin-=isoquinoline; Meim=methylimidazole. The biological assays were performed as previously described by method of Hacker et al. *Cancer Research*, 1985, 45, 4748. Complexes were all dissolved in 10% DMSO.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A bis(platinum) complex having the structure:

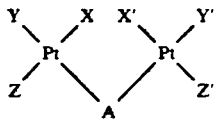

wherein X, Y, Z, X', Y' and Z' are the same or different ligands and are an anionic group selected from the group consisting of halide, pseudohalide, substituted pseudohalide, sulphate, phosphate, phosphonate, nitrate, carboxylate, substituted carboxylate, dicarboxylate and substituted dicarboxylate or a neutral group which may be substituted or unsubstituted and is selected from the group consisting of primary or secondary amines, sulfoxide and phosphine, with the proviso that if Y, Y', Z, and Z' are halide, sulphate, phosphate, nitrate, carboxylate, substituted carboxylate or dicarboxylate, then X and X' cannot be a primary or secondary amine and A is a diamine or polyamine wherein the primary amine N atoms are coordinated to the Pt atom such that platinum is present at Pt²⁺.

2. The bis(platinum) complex according to claim 1 wherein A has the formula:

NDE—(C(R⁴)₂)ᵣ—(R⁵)ₒ—(C(R⁶)₂)ₚ—NDE wherein r and p are integers from 1 to 4, inclusive, and o is 0 or 1; R⁴ and R⁶ are the same or different and are hydrogen, lower alkyl, aryl, cycloalkyl, cycloalkenyl, aralkyl, halogen, pseudohalogen, hydroxy, alkoxy, aryloxy, carboxylic ester, or carboxylic acid salt; D and E are the same or different and are hydrogen, lower alkyl, aryl, alkaryl, aralkyl, alkenyl, cycloalkyl, cycloalkenyl, halogen, pseudohalogen, hydroxy, alkoxy, aryloxy, sulphonic acid, or sulphonic acid salt; and R⁵ is alkyl, aryl, amino, alkylamino, diamino of the formula:

—(NH(CH₂)ᵩNH)— wherein q is an integer of 1 to 4, inclusive, hydroxyalkyl, alkoxy, sulfur or oxygen.

3. A bis(platinum) complex having the structure:

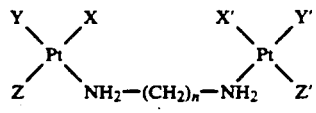

wherein X, Y, Z, X', Y', and Z' are the same or different ligands and are selected from an anionic group selected from the group consisting of halide, pseudohalide, substituted pseudohalide, sulphate, phosphate, phosphonate, nitrate, carboxylate, substituted carboxylate, dicarboxylate, and substituted carboxylate or a neutral group which may be substituted or unsubstituted and is elected from the group consisting of primary or secondary and phosphine, with the proviso that if Y, Y', Z, and Z' are halide, sulphate, phosphate, nitrate, carboxylate, substituted carboxylate or dicarboxylate, then X and X' cannot be a primary or secondary amine and wherein n is an integer of 2 to 20 inclusive.

4. The complex of claim 3 wherein Y and Y' are chlorine and X, X', Z, and Z' are all amines.

5. The complex of claim 3 wherein X and X' are chlorine and Y, Z, Y' and Z' are amines.

6. The complex of claim 3 wherein Y and X' are chlorine and X, Z, Y' and Z' are amines.

7. The complex of claim 3 wherein Y, Z, X', and Z' are all chlorine and X and Y' are amines.

8. The complex of claim 3 wherein Y, Z and Y' are chlorine and X, X' and Z' are amines.

9. The complex of claim 3 wherein Y, Z and Z' are chlorine and X, X', and Y' are amines.

10. The complex of claim 3 wherein X, Z and Z' are chlorine and X, X', and Y' are amines.

11. The complex of claim 3 wherein X, Z and Y' are chlorine and X, X', and Y' are amines.

12. The complex of claim 3 wherein either X, Y, Z, X' Y' or Z' is a carboxylate or substituted carboxylate of the formula:

CR³(C(R³)₂)ₘCO₂ wherein m is an integer from 0 to 5, inclusive; and the R³ groups are the same or different and is hydrogen, substituted or unsubstituted straight or branched alkyl, aryl, alkaryl, alkenyl, cycloalkyl, cycloalkenyl, halogen, pseudohalogen, hydroxy, carbonyl, formyl, nitro, amides, amino, alkoxy, aryloxy, sulphonic acid salt, carboxylic acid ester or carboxylic acid salt.

13. A process for producing a bis(platinum) complex, said process comprising:

(a) reacting a compound of the formula RNH₃⁺Cl wherein RNH₃ represents PtX'Y'Z'A wherein Z', Y', Z' and A are as defined in claim 1 with a compound of the formula:

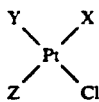

wherein X, Y and Z are as defined in claim 1 in the presence of a base;

and (b) recovering a compound of the formula:

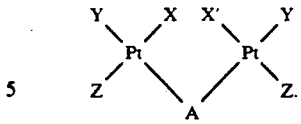

14. A pharmaceutical composition comprising a tumor-inhibiting effective amount of a complex according to claim 1 in a pharmaceutically acceptable carrier.

15. A method of inhibiting tumor growth in a mammal, said method comprising administering a tumor-inhibiting effective amount of a complex according to claim 1.

16. A pharmaceutical composition comprising a tumor-inhibiting effective amount of a complex according to claim 3 in a pharmaceutically acceptable carrier.

17. A method of inhibiting tumor growth in a mammal, said method comprising administering a tumor-inhibiting effective amount of a complex according to claim 3.

* * * * *